(12) United States Patent
Buehler et al.

(10) Patent No.: US 10,269,507 B2
(45) Date of Patent: Apr. 23, 2019

(54) HYBRID SUPERCAPACITOR, INCLUDING AN ELECTROLYTE COMPOSITION, HAVING IMPROVED CONDUCTIVITY

(71) Applicant: Robert Bosch GmbH, Stuttgart (DE)

(72) Inventors: Elisabeth Buehler, Tamm (DE); Mathias Widmaier, Magstadt (DE); Severin Hahn, Kirchheim Unter Teck (DE); Thomas Eckl, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/609,328

(22) Filed: May 31, 2017

(65) Prior Publication Data

US 2017/0352498 A1    Dec. 7, 2017

(30) Foreign Application Priority Data

Jun. 1, 2016  (DE) .................. 10 2016 209 594

(51) Int. Cl.
*H01G 11/64* (2013.01)
*C07D 295/26* (2006.01)
(Continued)

(52) U.S. Cl.
CPC ........... *H01G 11/64* (2013.01); *C07D 295/26* (2013.01); *H01G 11/02* (2013.01); *H01G 11/04* (2013.01);
(Continued)

(58) Field of Classification Search
None
See application file for complete search history.

(56) References Cited

U.S. PATENT DOCUMENTS 5,849,432 A   12/1998  Angell et al.
8,081,418 B2  12/2011  Brandon et al.
(Continued)

FOREIGN PATENT DOCUMENTS

EP   1187244 A2    3/2002
WO   2014073712 A1  5/2014

OTHER PUBLICATIONS

Hernandez, et al. "Chemical Mechanical Polishing of Al and SiO2 Thin Films: The Role of Consumables", J. of The Electrochemical Society, 146 (12), (1999), pp. 4647-4653.
(Continued)

*Primary Examiner* — Dion Ferguson
(74) *Attorney, Agent, or Firm* — Norton Rose Fulbright US LLP; Gerard Messina

(57) ABSTRACT

A hybrid supercapacitor, including at least one negative electrode that includes a statically capacitive active material, an electrochemical redox active material, or a mixture thereof, at least one positive electrode that includes a statically capacitive active material, an electrochemical redox active material, or a mixture thereof, at least one separator that is situated between the at least one negative electrode and the at least one positive electrode, and an electrolyte composition, with the condition that at least one electrode includes a statically capacitive active material, and at least one electrode includes an electrochemical redox active material, the electrolyte composition being a liquid electrolyte composition and including at least one liquid, aprotic, organic solvent, at least one conducting salt, and at least one additive.

10 Claims, 1 Drawing Sheet

(51) Int. Cl.
H01G 11/04 (2013.01)
H01G 11/52 (2013.01)
H01G 11/60 (2013.01)
H01G 11/62 (2013.01)
H01G 11/02 (2013.01)

(52) U.S. Cl.
CPC .............. *H01G 11/52* (2013.01); *H01G 11/60* (2013.01); *H01G 11/62* (2013.01); *Y02E 60/13* (2013.01)

(56) References Cited

U.S. PATENT DOCUMENTS 8,586,250 B2  11/2013  Iwaya
2010/0040954 A1*  2/2010  Amine ................. H01G 9/038
429/322

OTHER PUBLICATIONS

Sun, et al. "A Novel Lithium Batttery Electrolyte Based on Lithium Fluoride and a Tris(pentafluorophenyl) Borane Anion Receptor in DME", Electrochemical and Sikud-State Leters, 1(6), (1998), pp. 239-240.

Sun, et al. "Using a Boron-Based Anion Receptor Additive to Improve the Thermal Stability of LiPF6-Based Electrolyte for Lithium Batteries", Electrochemical and Solid-State Letters, 5 (11), (2002), pp. A248-A251.

Lee et al., "The Synthesis of New Family of Anion Receptors and the Studies of Their Effect on Ion Pair Dissocation and Conductivity of Lithium Salts in Nonaqueous Solutions". J. Electrochem. Soc., 143, 1996, 12, 3825-3829.

Lee et al., "Synthesis of Cyclic Aza-Ether Compounds and Studies of Their Use as Anion Receptors in Nonaqueous Lithium Halide Salts Solution" J. Electrochem. Soc., 146, 2000, 1, 9-14.

Zhang et al., "A Novel Electrolyte Solvent for Rechargeable Lithium and Lithium-Ion Batteries" The Electrochemical Society, Dec. 1996, 4047-4053, 143-12.

Lee et al., "The Synthesis of a New Family of Boron-Based Anion Receptors and the Study of Their Effect on Ion Pair Dissociation and Conductivity of Lithium Salts in Nonaqueous Solutions" Aug. 1998, 2813- 2817, 8-145, The Electrochemical Society.

Sun et al., "The Compatibility of a Boron-Based Anion Receptor with the Carbon Anode in Lithium-Ion Batteries" 2003, A43-A46, 6-2, Electrochemical and Solid State Letters.

Zhang, "A review on electrolyte additives for lithium-ion batteries" 2006, 1379-1394, 162, Journal of Power Sources.

Lee et al., "Synthesis and Study of New Cyclic Boronate Additives for Lithium Battery Electrolytes" 2002, A1460-A1465, 49-11, The Electrochemical Society.

Sun et al., "Improved Elevated Temperature Cycling of LiMn2O4 Spinel Through the Use of a Composite LiF-Based Electrolyte" 2001, A184-A186, 4-11, Electrochemical and Solid State Letters.

Lee et al., "Synthesis of a Series of Fluorinated Boronate Compounds and Their Use as Additives in Lithium Battery Electrolytes" 2004, A1429-A1435, 151-9, Journal of the Electrochemical Society.

Sun et al., "A New Additive for Lithium Battery Electrolytes Based on an Alkyl borate Compound" 2002, A355-A359, 149-3, Journal of the Electrochemical Society.

* cited by examiner

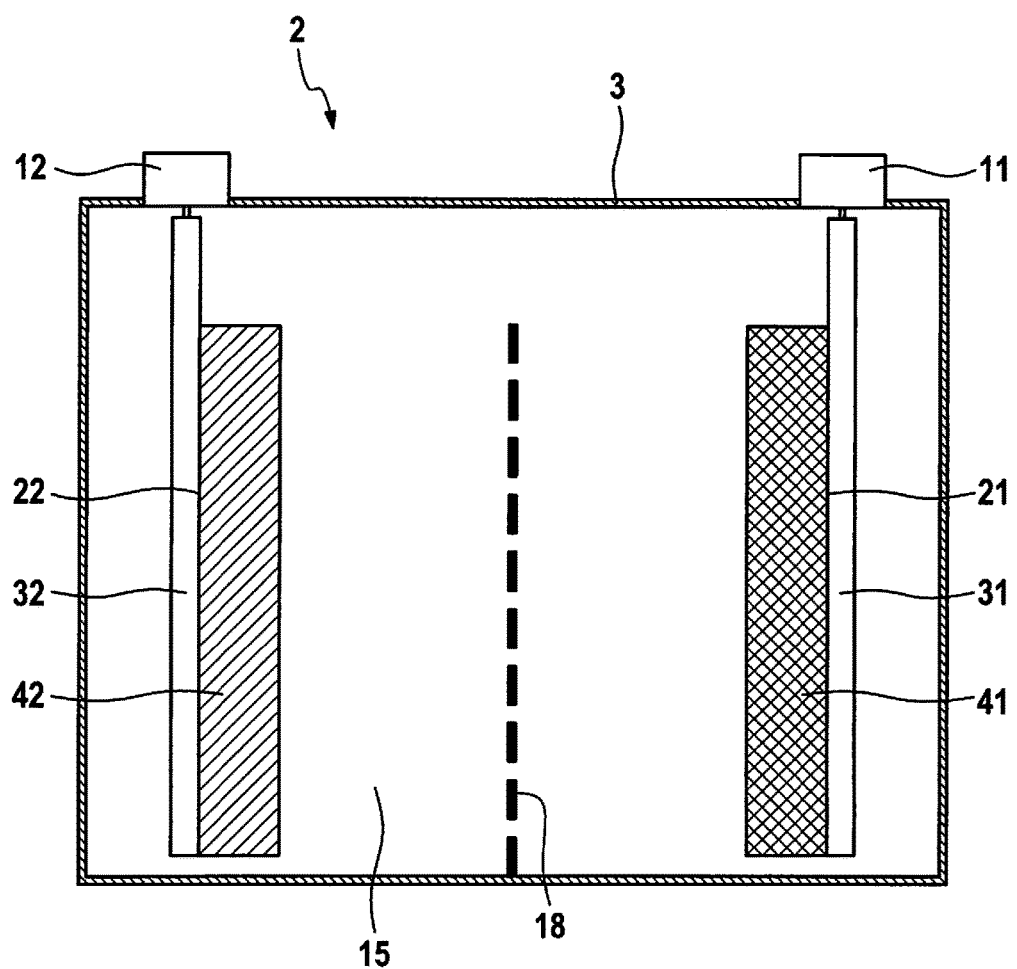

HYBRID SUPERCAPACITOR, INCLUDING AN ELECTROLYTE COMPOSITION, HAVING IMPROVED CONDUCTIVITY

CROSS REFERENCE

The present application claims the benefit under 35 U.S.C. § 119 of German Patent Application No. DE 102016209594.3 filed on Jun. 1, 2016, which is expressly incorporated herein by reference in its entirety.

BACKGROUND INFORMATION

The storage of electrical energy with the aid of electrochemical energy storage systems such as electrochemical capacitors (supercapacitors) or electrochemical primary or secondary batteries has been available for many years. These energy storage systems differ in their underlying principle of energy storage.

Supercapacitors generally include a negative electrode and a positive electrode that are separated from one another by a separator. In addition, an ion-conductive electrolyte is situated between the electrodes. The storage of electrical energy is based on the fact that when a voltage is applied to the electrodes of the supercapacitor, an electrochemical double layer forms on the surfaces of the electrodes. This double layer is formed from solvated charge carriers from the electrolyte, which become arranged on the surfaces of the oppositely electrically charged electrodes. In this type of energy storage, a redox reaction is not involved. Theoretically, supercapacitors may therefore be charged as often as desired, and thus have a very long service life. In addition, the power density of the supercapacitors is high, whereas the energy density is rather low compared to lithium-ion batteries, for example.

In contrast, the energy storage in primary and secondary batteries takes place via a redox reaction. These batteries also generally include a negative electrode and a positive electrode that are separated from one another by a separator. An ion-conductive electrolyte is likewise situated between the electrodes. In lithium-ion batteries, one of the most commonly used secondary battery types, the energy storage takes place via the intercalation of lithium ions into the electrode active materials. During operation of the battery cell, i.e., during a discharging operation, electrons flow in an external circuit from the negative electrode to the positive electrode. During a discharging operation, lithium ions migrate from the negative electrode to the positive electrode within the battery cell. In the process, the lithium ions are reversibly deintercalated from the active material of the negative electrode, also referred to as delithiation. During a charging operation of the battery cell, the lithium ions migrate from the positive electrode to the negative electrode. In the process, the lithium ions are reversibly reintercalated into the active material of the negative electrode, also referred to as lithiation.

Lithium-ion batteries are characterized in that they have a high energy density; i.e., they are able to store a large quantity of energy per mass or volume. However, in return they have only a limited power density and service life. This is disadvantageous for many applications, so that lithium-ion batteries cannot be used, or can be used only to a limited extent, in these areas.

Hybrid supercapacitors represent a combination of these technologies, and are suitable for closing the gap between the application options in lithium ion battery technology and supercapacitor technology.

Hybrid supercapacitors generally likewise include two electrodes, which in each case include a current collector and are separated from one another by a separator. The transport of the electrical charges between the electrodes is ensured by electrolytes or electrolyte compositions. As active material, the electrodes generally include a conventional supercapacitor material (also referred to below as statically capacitive active material) and a material that is capable of entering into a redox reaction with the charge carriers of the electrolyte and forming an intercalation compound therefrom (also referred to below as electrochemical redox active material). The energy storage principle of the hybrid supercapacitors is thus based on the formation of an electrochemical double layer in combination with the formation of a Faraday lithium intercalation compound. The energy storage system thus obtained has a high energy density, and at the same time, a high power density and a long service life.

However, the performance of conventional hybrid supercapacitors is often limited by the conductivity of the electrolyte composition. In particular in the area of electromobility, there is a need for energy storage systems that have preferably high performance.

The use of electrolyte additives in electrolyte compositions to improve the properties of lithium-ion batteries is described in the related art, for example in Journal of Power Sources 162 (2006) 1379-1394. Electrolyte additives, which are used to improve the ion solvation in electrolyte compositions of lithium-ion batteries, are described, for example, in Zhang, Journal of Power Sources 162 (2006) 1379-1394; Lee et al., J. Electrochem. Soc. 145 (1998) 2813; Sun et al., J. Electrochem. Soc. 146 (1999) 3655; Zhang et al., J. Electrochem. Soc. 143 (1996) 4047; Angell, U.S. Pat. No. 5,849,432 (1998); Sun et al., J. Electrochem. Soc. 149 (2002) A355; Sun et al., Electrochem. Solid-State Lett. 1 (1998) 239; Sun et al., Electrochem. Solid-State Lett. 4 (2001) A184; Sun et al., Electrochem. Solid-State Lett. 5 (2002) A248; Sun et al., Electrochem. Solid-State Lett. 6 (2003) A43; Lee et al., J. Electrochem. Soc. 149 (2002) A1460; Lee et al., J. Electrochem. Soc. 151 (2004) A1429; Lee et al., J. Electrochem. Soc. 143 (1996) 3825; and Lee et al., J. Electrochem. Soc. 147 (2000) 9.

U.S. Pat. No. 8,081,418 describes a double layer capacitor that includes an electrolyte composition to which an additive for lowering the melting point of the electrolyte composition is added in order to improve the use at low temperatures.

U.S. Pat. No. 8,586,250 describes, among other things, a nonaqueous electrolyte composition for a lithium ion capacitor, including a lithium salt, and a solvent mixture of a hydrofluoro ether of formula $CF_3CH_2OCF_2CF_2H$ and a carbonate solvent. The solvent mixture is used for improved solvation of the lithium salt at low temperatures.

An object of the present invention is to provide an electrochemical energy storage system having improved conductivity via an electrolyte composition.

SUMMARY

The present invention relates to a hybrid supercapacitor, including
 at least one negative electrode that includes a statically capacitive active material, an electrochemical redox active material, or a mixture thereof,
 at least one positive electrode that includes a statically capacitive active material, an electrochemical redox active material, or a mixture thereof, at least one separator that is situated between the at least one negative electrode and the at least one positive electrode, and an electrolyte composition, with the condition that at least one electrode includes a statically capacitive active material, and at least one electrode includes an electrochemical redox active material, the electrolyte composition being a liquid electrolyte composition and including at least one liquid, aprotic, organic solvent, at least one conducting salt, composed of at least one cation and at least one anion, that is suitable for balancing the charge of the cation, and at least one additive, selected from at least one Lewis acid, that is suitable for forming a complex compound with the at least one anion.

The hybrid supercapacitor according to the present invention includes at least one positive electrode and at least one negative electrode. The electrodes each include an electrically conducting current collector, also referred to as a collector, and an active material that is applied thereto. The current collector includes copper or aluminum, for example, as the electrically conducting material. In one preferred specific embodiment, the current collector of the electrodes is made of aluminum.

A negative active material is applied to the negative electrode. The negative active material includes a statically capacitive active material, an electrochemical redox active material, or a mixture thereof.

Within the meaning of the present invention, a statically capacitive active material is a material that is known from conventional double layer-electrodes, and that is suitable for forming a static double layer capacitor, in particular due to the formation of a Helmholtz layer. It is designed in such a way that a preferably large surface for forming the electrochemical double layer results. The most commonly used electrode material for supercapacitors is carbon in its various forms, such as activated carbon (AC), activated carbon fibers (ACF), carbide-derived carbon (CDC), carbon aerogel, graphite (graphene), and carbon nanotubes (CNTs). These electrode materials are suitable within the scope of the present invention as statically capacitive electrode active materials. Carbon modifications, in particular activated carbon, are preferably used.

Within the meaning of the present invention, an electrochemical redox active material is a material that is known from electrochemical secondary batteries, in particular lithium-ion batteries, and that is suitable for entering into a reversible electrochemical or Faraday lithium ion intercalation reaction or for forming a lithium ion intercalation compound.

Suitable electrochemical redox active materials for the negative electrode are in particular lithium titanates such as $Li_4Ti_5O_{12}$, or also lithium vanadium phosphates such as $Li_3V_2(PO_4)_3$.

In one preferred specific embodiment, the negative electrode includes a mixture of statically capacitive active material and electrochemical redox active material, for example a mixture of activated carbon and $Li_4Ti_5O_{12}$. The ratio of capacitive active material to electrochemical redox active material is preferably in a range of 1:0.25 to 1:1.25.

A positive active material is applied to the positive electrode. The positive active material includes a statically capacitive active material, an electrochemical redox active material, or a mixture thereof.

All statements concerning the negative electrode correspondingly apply to the statically capacitive material of the positive electrode. The active materials mentioned for the negative electrode are also suitable for the positive electrode.

Suitable electrochemical redox active materials for the positive electrode are, for example, lithiated intercalation compounds that are capable of reversibly absorbing and releasing lithium ions. The positive active material may include a combined oxide containing at least one metal selected from the group made up of cobalt, magnesium, nickel, and lithium.

One specific embodiment of the present invention contains an active material of the positive electrode, including a compound of formula $LiMO_2$, where M is selected from Co, Ni, Mn, Cr, or mixtures thereof, and mixtures of same with Al. $LiCoO_2$ and $LiNiO_2$ are to be mentioned in particular.

In one preferred specific embodiment, the cathode active material is a material that includes nickel, i.e., $LiNi_{1-x}M'_xO_2$, where M' is selected from Co, Mn, Cr, and Al, and $0 \leq x < 1$. Examples include lithium-nickel-cobalt-aluminum oxide cathodes (for example, $LiNi_{0.8}Co_{0.15}Al_{0.05}O_2$; NCA) and lithium-nickel-manganese-cobalt oxide cathodes (for example, $LiNi_{0.8}Co_{0.15}Al_{0.05}O_2$; NMC (811) or $LiNi_{0.33}Mn_{0.33}Co_{0.33}O_2$; NMC (111)).

Also to be mentioned as preferred positive active materials are superlithiated layered oxides, which are known to those skilled in the art. Examples of such are $Li_{1+x}Mn_{2-y}M_yO_4$, where $x \leq 0.8$, $y < 2$; $Li_{1+x}Co_{1-y}M_yO_2$, where $x \leq 0.8$, $y < 1$; and $Li_{1+x}Ni_{1-y-z}Co_yM_zO_4$, where $x \leq 0.8$, $y < 1$, $z < 1$, and $y+z < 1$. M may be selected from Al, Mg, and/or Mn in the above-mentioned compounds.

Two or more of the positive active materials may in particular also be used in combination with one another. One preferred specific embodiment includes, for example, compounds of formula $n(Li_2MnO_3)$: $n-1$ $(LiNi_{1-x}M'_xO_2)$, where M' is selected from Co, Mn, Cr, and Al, and $0 < n < 1$ and $0 < x < 1$.

Also emphasized in particular as suitable positive active materials are spinel compounds ($LiMn_2O_4$, for example), olivine compounds ($LiFePO_4$, for example), silicate compounds ($Li_2FeSiO_4$, for example), tavorite compounds ($LiVPO_4F$, for example), $Li_2MnO_3$, $Li_{1.17}Ni_{0.17}Co_{0.1}Mn_{0.56}O_2$, and $Li_3V_2(PO_4)_3$.

In one preferred specific embodiment, the positive electrode includes a mixture of statically capacitive active material and electrochemical redox active material, for example a mixture of activated carbon and $LiMn_2O_4$. The ratio of capacitive active material to electrochemical redox active material is preferably in a range of 1:0.25 to 1:1.25.

As further components, the negative active material and/or the positive active material may include in particular binders such as styrene-butadiene copolymer (SBR), polyvinylidene fluoride (PVDF), polytetrafluoroethene (PTFE), carboxymethylcellulose (CMC), polyacrylic acid (PAA), polyvinyl alcohol (PVA), and ethylene propylene diene terpolymer (EPDM) in order to increase the stability of the electrodes. In addition, conductive additives such as conductive carbon black or graphite may be added.

The task of the separator is to protect the electrodes from direct contact with one another, thus preventing a short circuit. At the same time, the separator must ensure the transfer of the ions from one electrode to the other. Suitable materials are characterized in that they are formed from an insulating material having a porous structure. Suitable materials are in particular polymers such as cellulose, polyolefins, polyesters, and fluorinated polymers. Particularly preferred polymers are cellulose, polyethylene (PE), polypropylene (PP), polyethylene terephthalate (PET), polytetrafluoroethene (PTFE), and polyvinylidene fluoride (PVDF). In addition, the separator may include ceramic materials or may be made of same, provided that a substantial (lithium) ion transfer is ensured. Ceramics that include MgO or $Al_2O_3$ are to be mentioned in particular as materials. The separator may be made of a layer of one or more of the materials mentioned above, or also of multiple layers in which in each case one or more of the mentioned materials are combined with one another.

In addition, the hybrid supercapacitor includes an electrolyte composition that includes at least one aprotic, organic solvent that is liquid under the conditions that typically prevail in electrochemical energy storage systems during operation (i.e., at a temperature in a range of −40° C. to 100° C., in particular 0° C. to 60° C., and at a pressure in a range of 0.5 bar to 5 bar, in particular 0.8 bar to 2 bar), at least one conducting salt composed of at least one cation and at least one anion, and at least one additive, selected from at least one Lewis acid, that is suitable for forming a complex compound with the at least one anion.

In the present context, "liquid" means that the solvent has a viscosity η of ≤100 mPa·s, in particular ≤10 mPa·s. The viscosity η is preferably in a range of 0.01 mPa·s to 8 mPa·s, in particular in a range of 0.1 mPa·s to 5 mPa·s.

Suitable solvents have sufficient polarity for dissolving the further components of the electrolyte composition, in particular the conducting salt or the conducting salts. Acetonitrile, tetrahydrofuran, diethyl carbonate, or γ-butyrolactone, as well as cyclic and acyclic carbonates, in particular propylene carbonate, ethylene carbonate, dimethyl carbonate, diethyl carbonate, ethylene methyl carbonate, ethyl methyl carbonate, and mixtures thereof are to be mentioned as examples. Acetonitrile, propylene carbonate, ethylene carbonate, dimethyl carbonate, diethyl carbonate, ethylene methyl carbonate, ethyl methyl carbonate, and mixtures thereof are particularly preferred.

In addition, the electrolyte composition includes at least one conducting salt. Salts with sterically sophisticated anions and optionally sterically sophisticated cations are particularly suited. Examples of such are tetraalkylammonium borates such as $N(CH_3)_4BF_4$. However, in particular lithium salts are one particularly suitable class of conducting salts. The conducting salt may be selected, for example, from the group made up of lithium chlorate ($LiClO_4$), lithium tetrafluoroborate ($LiBF_4$), lithium hexafluorophosphate ($LiPF_6$), lithium hexafluoroarsenate ($LiAsF_6$), lithium trifluoromethanesulfonate ($LiSO_3CF_3$), lithium bis(trifluoromethylsulfonyl) imide ($LiN(SO_2CF_3)_2$), lithium bis(pentafluoroethylsulfonyl) imide ($LiN(SO_2C_2F_5)_2$), lithium bis (oxalato) borate (LiBOB, $LiB(C_2O_4)_2$), lithium difluoro (oxalato) borate ($LiBF_2(C_2O_4)$), lithium tris (pentafluorethyl) trifluorophosphate ($LiPF_3(C_2F_5)_3$), and combinations thereof.

It has been found that adding at least one Lewis acid that is suitable for forming a complex compound with the at least one anion of the electrolyte composition increases the conductivity of the electrolyte composition. This is achieved due to the fact that the anion of the conducting salt forms a complex compound with the Lewis acid, in which the anion coordinates with the Lewis acid. The charge density of the anion is thus reduced, and the formation of ion pairs from the cation and the anion of the conducting salt in the electrolyte composition is effectively reduced.

In one specific embodiment of the present invention, the at least one additive includes a Lewis acid selected from a boron(III) compound and an aluminum(III) compound, and mixtures thereof. The boron(III) compound and the aluminum(III) compound are configured in such a way that the free valence electron of the anions of the conducting salt may coordinate with the boron atom or the aluminum atom. Boranes, boric acid, boric acid esters, boronic acid, boronic acid esters, borinic acid, borinic acid esters, and boron halides are to be mentioned as examples. Further examples are aluminum halides, aluminum alkyls, aluminum alkoxides, and aluminum alkyl alkoxides.

In one preferred specific embodiment, the at least one additive includes a boron(III) compound of formula (I):

(I)

where
R, R', and R" may be independently selected from:
a hydrogen atom,
a halogen atom, in particular a chlorine or fluorine atom,
a hydroxy group,
a linear or branched, preferably linear, saturated or unsaturated, preferably saturated, hydrocarbon moiety having 1 to 18, preferably 1 to 12, in particular 1 to 6, carbon atoms, which may optionally be substituted with halogen atoms, in particular fluorine atoms,
a cyclic, saturated or unsaturated, preferably saturated, hydrocarbon moiety having 3 to 18, preferably 5 to 12, in particular 5, 6, or 7, carbon atoms, which may optionally be substituted with halogen atoms, in particular fluorine atoms, or with linear saturated alkyl moieties having 1 to 3 carbon atoms,
an aromatic hydrocarbon moiety having 6 to 18, preferably 6 to 12, in particular 6 to 9, carbon atoms, which may optionally be substituted with halogen atoms, in particular fluorine atoms, or with linear, completely or partially fluorinated, preferably perfluorinated, saturated alkyl moieties having 1 to 3 carbon atoms, and
a moiety —OR, where R has the meaning defined above, and
where adjacent moieties R, R', R" may optionally be joined together to form a cyclic compound.

In one specific embodiment, the boron(III) compound of formula (I) is a borane of formula (I-a):

(I-a)

where
$R^1$, $R^2$, and $R^3$ may be independently selected from:
a hydrogen atom,
a linear or branched, preferably linear, saturated hydrocarbon moiety having 1 to 12, in particular 1 to 6, carbon atoms, which may optionally be substituted with fluorine atoms, and
an aromatic hydrocarbon moiety having 6 to 12, in particular 6 to 9, carbon atoms, which may optionally be substituted with moieties selected from —F, —$CF_3$, and —$C_2F_5$, and where adjacent moieties $R^1$, $R^2$, and $R^3$ may optionally be joined together to form a cyclic compound.

In one preferred specific embodiment, at least two of moieties $R^1$, $R^2$, and $R^3$ are identical. In one particularly preferred specific embodiment, moieties $R^1$, $R^2$, and $R^3$ are identical.

$R^1$, $R^2$, and $R^3$ are, for example, independently selected from —$CF_3$, —$C_2F_5$, —$C_3F_7$, —$CF(CF_3)_2$, —$CH(CF_3)_2$, —$C_4F_9$, —$CF_2CF(CF_3)_2$, —$CH_2CH(CF_3)_2$, —$C_6F_5$, —$C_6H_3(CF_3)_2$, —$C_6H_2(CF_3)_3$. Preferred examples include pentafluorophenyl moieties (—$C_6F_5$), 3,5-bis-(trifluoromethyl)phenyl moieties (—$C_6H_3(CF_3)_2$), and 2,4,6-tris-(trifluoromethyl)phenyl moieties (—$C_6H_2(CF_3)_3$).

In another specific embodiment, the boron(III) compound of formula (I) is a boric acid ester of formula (I-b):

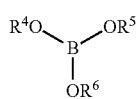

(I-b)

where $R^4$, $R^5$, and $R^6$ may be independently selected from:

a hydrogen atom, a linear or branched, preferably linear, saturated hydrocarbon moiety having 1 to 12, in particular 1 to 6, carbon atoms, which may optionally be substituted with fluorine atoms, and an aromatic hydrocarbon moiety having 6 to 12, in particular 6 to 9, carbon atoms, which may optionally be substituted with moieties selected from —F, —$CF_3$, and —$C_2F_5$, and where adjacent moieties $R^4$, $R^5$, and $R^6$ may optionally be joined together to form a cyclic compound.

In one preferred specific embodiment, at least two of moieties $R^4$, $R^5$, and $R^6$ are identical. In one particularly preferred specific embodiment, moieties $R^4$, $R^5$, and $R^6$ are identical.

$R^4$, $R^5$, and $R^6$ are, for example, independently selected from —$CF_3$, —$C_2F_5$, —$C_3F_7$, —$CF(CF_3)_2$, —$CH(CF_3)_2$, —$C_4F_9$, —$CF_2CF(CF_3)_2$, —$CH_2CH(CF_3)_2$, —$C_6F_5$, —$C_6H_3(CF_3)_2$, —$C_6H_2(CF_3)_3$. Preferred examples include pentafluorophenyl moieties (—$C_6F_5$), 3,5-bis-(trifluoromethyl)phenyl moieties (—$C_6H_3(CF_3)_2$), and 2,4,6-tris-(trifluoromethyl)phenyl moieties (—$C_6H_2(CF_3)_3$).

In another specific embodiment, the boron(III) compound of formula (I) is a boronic acid ester of formula (I-c):

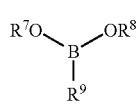

(I-c)

where $R^7$, $R^8$, and $R^9$ may be independently selected from:

a hydrogen atom, a linear or branched, preferably linear, saturated hydrocarbon moiety having 1 to 12, in particular 1 to 6, carbon atoms, which may optionally be substituted with fluorine atoms, and an aromatic hydrocarbon moiety having 6 to 12, in particular 6 to 9, carbon atoms, which may optionally be substituted with moieties selected from —F, —$CF_3$, and —$C_2F_5$, and where adjacent moieties $R^7$, $R^8$, and $R^9$ may optionally be joined together to form a cyclic compound.

In one preferred specific embodiment, moieties $R^7$ and $R^6$ are identical. In one particularly preferred specific embodiment, moieties $R^7$ and $R^8$ are joined together and form a ring structure.

$R^7$, $R^8$, and $R^9$ are, for example, selected from —$CF_3$, —$C_2F_5$, —$C_3F_7$, —$CF(CF_3)_2$, —$CH(CF_3)_2$, —$C_4F_9$, —$CF_2CF(CF_3)_2$, —$CH_2CH(CF_3)_2$, —$C_6F_5$, —$C_6H_3(CF_3)_2$, —$C_6H_2(CF_3)_3$. Preferred examples include pentafluorophenyl moieties (—$C_6F_5$), 3,5-bis-(trifluoromethyl)phenyl moieties (—$C_6H_3(CF_3)_2$), and 2,4,6-tris-(trifluoromethyl)phenyl moieties (—$C_6H_2(CF_3)_9$).

Examples of suitable boron(III) compounds are the boranes $B(CF_3)_3$, $BH(CF_3)_2$, $B(C_6H_5)(CF_3)_2$, $B(C_6F_5)_3$, the boric acid esters $B(OC_6H_5)_3$, $B(OC_6H_4F)_3$, $B(OC_6H_3F_2)_3$, $B(OC_6H_2F_3)_3$, $B(OC_6HF_4)_3$, $B(OC_6F_5)_3$, $B(OC_6H_4(CF_3))_3$, $B(OC_6H_3(CF_3)_2)_3$, $B(OCH(CF_3)_2)$, and the boronic acid esters $B(C_6F_5)(O_2C_6F_4)$, $B(C_6F_5)(O_2C_2(CF_3)_4)$, $BF(O_2C_2H_4)$, $BF(O_2CH_2CH(CH_3))$.

In another specific embodiment of the present invention, the at least one additive includes a Lewis acid selected from a polydentate nitrogen compound. The nitrogen compound is configured in such a way that the anions of the conducting salt may coordinate with the nitrogen atoms. To achieve this, the nitrogen atoms each bear at least one electron-attracting group. An electron deficit is thus created on the nitrogen, and the Lewis acidity of the nitrogen increases. The polydentate nitrogen compounds may be represented by the following formula (II):

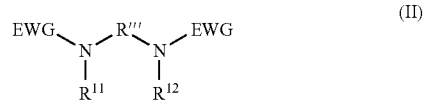

(II)

where

R''' represents an alkylene group —$(CH_2)_n$— having 1 to 10 carbon atoms (n=1 to 10), which may optionally be substituted with at least one linear alkyl moiety having 1 to 6, in particular 1 to 3, carbon atoms, and/or at least one halogen atom;

EWG represents an electron-attracting group; and $R^{11}$, $R^{12}$ independently represent a hydrogen atom, a linear or branched, preferably linear, saturated or unsaturated, preferably saturated, alkyl moiety having 1 to 6 carbon atoms, an aryl moiety having 6 to 12 carbon atoms, or a moiety —R'''—$NR^3$(EWG), where R''' and EWG have the meanings defined above, and $R^3$ represents a further group $R^{11}$ or a further group R''', with the condition that $R^{11}$ and $R^{12}$ are joined together via this alkylene group R''' to form a cyclic compound.

In one specific embodiment, R''' represents an unsubstituted alkylene group, in particular an alkylene group having 1 to 6 carbon atoms. Examples are a methylene group —$(CH_2)$—, an ethylene group —$(C_2H_4)$—, a propylene group —$(C_3H_6)$—, a butylene group —$(C_4H_8)$—, a pentylene group —$(C_5H_{10})$—, and a hexylene group —$(C_6H_{12})$—.

Within the meaning of the present invention, an electron-attracting group EWG is a group that has a charge-altering, inductive effect on adjacent atoms or molecular portions and thus reduces the electron density in the adjacent atom or molecular portion (so-called "−I effect").

In one specific embodiment, electron-attracting group EWG is selected from halides and sulfonic acid groups. Sulfonic acid groups of formulas

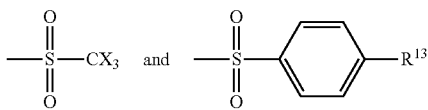

are preferred, where X represents a hydrogen atom or a halogen atom, in particular a fluorine atom and/or a chlorine atom, and $R^{13}$ represents a hydrogen atom, a halogen atom, in particular a fluorine, chlorine, and/or bromine atom, an optionally halogenated alkyl moiety having 1 to 4 carbon atoms, or a nitro group ($-NO_2$).

In one preferred specific embodiment, X is a hydrogen atom or a fluorine atom, and $R^{13}$ is a bromine atom, a methyl group, a trifluoromethyl group, or a nitro group.

Electron-attracting groups EWG selected from a tosyl group ($-SO_2-C_6H_4-CH_3$), a mesyl group ($-SO_2-CH_3$), and a triflyl group ($-SO_2-CF_3$) are particularly preferred.

Particularly preferred polydentate nitrogen compounds are cyclic nitrogen compounds having at least four, in particular four to seven, nitrogen atoms.

Examples of suitable preferred compounds are cyclic compounds of formula (III):

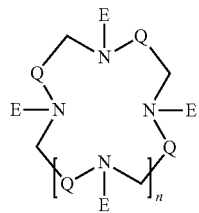

(III)

where

E represents an electron-attracting group selected from a tosyl group ($-SO_2-C_6H_4-CH_3$), a mesyl group ($-SO_2-CH_3$), and a triflyl group ($-SO_2-CF_3$);

Q represents an alkylene group of formula $-(CH_2)_m$ and m is an integer from 1 to 4; and n represents an integer from 1 to 4.

More highly preferred are compounds of the following formulas (III-a) through (III-d):

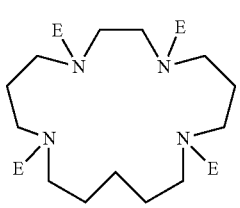

(III-a)

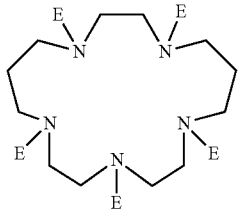

(III-b)

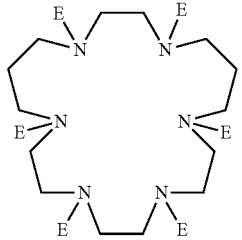

(III-c)

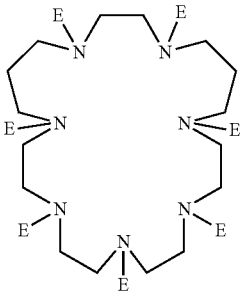

(III-d)

where E in each case is independently an electron-attracting group selected from a tosyl group ($-SO_2-C_6H_4-CH_3$), a mesyl group ($-SO_2-CH_3$), and a triflyl group ($-SO_2-CF_3$).

The electrolyte composition includes the at least one additive in a quantity of up to 10% by weight, preferably 0.1 to 9% by weight, in particular 0.5 to 5% by weight, for example 2% by weight, based on the total weight of the electrolyte composition.

The at least one additive is preferably added to the electrolyte composition in a quantity such that a molar ratio of conducting salt to additive of 1:0.5 to 1:5, preferably 1:1 to 1:3, in particular 1:1.2 to 1:2, is set.

In one specific embodiment of the present invention, the additive includes a combination of one of the boron(III) or aluminum(III) compounds described above with one of the polydentate nitrogen compounds described above.

In addition, the electrolyte composition may contain further additives that are suitable for improving the properties of the electrolyte composition, provided that the additives are sufficiently soluble in apolar solvents, and that the functions of the above-described components are not adversely affected by the presence of the additives. Suitable additives are known to those skilled in the art. For example, flame retardants, wetting agents, and agents that facilitate the formation of a preferred solid electrolyte interface (SEI) on the electrode surfaces may be added to the electrolyte composition. In particular, compounds having unsaturated hydrocarbon groups are to be mentioned here.

The additives are preferably contained in the electrolyte composition in a concentration of 0 to 3 mol/L, in particular 0.1 to 2 mol/L.

A further subject matter of the present invention relates to a liquid electrolyte composition for a hybrid supercapacitor, including at least one liquid, aprotic, organic solvent, at least one conducting salt, composed of at least one cation and at least one anion, that is suitable for balancing the charge of the cation, and at least one additive, selected from at least one Lewis acid, that is suitable for forming a complex compound with the at least one anion. The above discussion applies to the components. The liquid electrolyte composition may be advantageously used in a hybrid supercapacitor.

A hybrid supercapacitor according to the present invention is advantageously used in an electric vehicle (EV), in a hybrid vehicle (HEV), or in a plug-in hybrid vehicle (PHEV). The hybrid supercapacitor may be advantageously used in particular in recuperation systems. Further examples of use are tools and consumer electronics products. Tools are understood in particular to mean tools for home use and garden tools. Consumer electronics products are understood in particular to mean mobile telephones, tablet PCs, or notebooks.

The hybrid supercapacitor according to the present invention is characterized in that the solubility of the conducting salt in the aprotic, organic solvent of the electrolyte composition is significantly increased by adding a Lewis acid. This is achieved by the formation of complex compounds in which the anions of the conducting salt coordinate with the Lewis acid. In both cases, the charge density of the ions is reduced and the solubility is thus increased. The concentration of dissolved ions in the electrolyte composition increases due to the increased solubility. This results in an improvement of the conductivity of the electrolyte composition, thus achieving an improvement in the performance of the hybrid supercapacitor.

The increased conductivity of the electrolyte composition has the advantageous effect, in particular when the hybrid supercapacitor according to the present invention is used at low temperatures, for example at less than 10° C. or at less than 0° C., that the performance of the hybrid supercapacitor is improved compared to conventional hybrid supercapacitors. The low temperature behavior of the hybrid supercapacitor according to the present invention is thus improved.

BRIEF DESCRIPTION OF THE DRAWING

Specific embodiments of the present invention are described below with reference to the FIGURE.

FIG. 1 shows a schematic illustration of a hybrid supercapacitor.

DETAILED DESCRIPTION OF EXAMPLE EMBODIMENTS

A hybrid supercapacitor 2 is schematically illustrated in FIG. 1. Hybrid supercapacitor 2 includes a capacitor housing 3 having a prismatic design, in the present case a cuboidal design. In the present case, capacitor housing 3 has an electrically conductive design and is made of aluminum, for example. However, capacitor housing 3 may also be made of an electrically insulating material, for example plastic.

Hybrid supercapacitor 2 includes a negative terminal 11 and a positive terminal 12. A voltage provided by hybrid supercapacitor 2 may be tapped via terminals 11, 12. In addition, hybrid supercapacitor 2 may also be charged via terminals 11, 12. Terminals 11, 12 are situated spaced apart from one another on a top surface of prismatic capacitor housing 3.

An electrode winding which includes two electrodes, namely, a negative electrode 21 and a positive electrode 22, is situated within capacitor housing 3 of hybrid supercapacitor 2. Negative electrode 21 and positive electrode 22 each have a foil-like design, and are wound to form an electrode winding with a separator 18 situated in between. It is also possible to provide multiple electrode windings in capacitor housing 3. An electrode stack, for example, may be provided instead of the electrode winding.

Negative electrode 21 includes a negative active material 41 which has a foil-like design. Negative active material 41 has activated carbon (statically capacitive active material) as a base material, to which $Li_4Ti_5O_{12}$ (electrochemical redox active material) is applied. Negative electrode 21 includes a negative active material 41 which is present in particle form. Additives, in particular conductive carbon black and binder, are situated between the particles of negative active material 41. Negative active material 41 and the additives in each case form a composite which has a foil-like design.

Negative electrode 21 also includes a current collector 31, which likewise has a foil-like design. The composite of negative active material 41, the additives, and current collector 31 are placed flatly against one another and joined together. Current collector 31 of negative electrode 21 has an electrically conductive design and is made of a metal, for example copper. Current collector 31 of negative electrode 21 is electrically connected to negative terminal 11 of hybrid supercapacitor 2.

In the present case, positive electrode 22 includes a positive active material made of a mixture of activated carbon (statically capacitive active material) and $LiMn_2O_4$ (electrochemical redox active material). Positive electrode 22 includes a positive active material 42 which is present in particle form. Additives, in particular conductive carbon black and binder, are situated between the particles of positive active material 42. Positive active material 42 and the additives in each case form a composite which has a foil-like design.

Positive electrode 22 also includes a current collector 32 which likewise has a foil-like design. The composite, made up of positive active material 42, the additives, and current collector 32 are placed flatly against one another and joined together. Current collector 32 of positive electrode 22 has an electrically conductive design and is made of a metal, for example aluminum. Current collector 32 of positive electrode 22 is electrically connected to positive terminal 12 of hybrid supercapacitor 2.

Negative electrode 21 and positive electrode 22 are separated from one another by separator 18. Separator 18 likewise has a foil-like design. Separator 18 has an electronically insulating design, but is ionically conductive, i.e., is permeable for ions, in particular lithium ions.

Capacitor housing 3 of hybrid supercapacitor 2 is filled with a liquid electrolyte composition 15. Electrolyte composition 15 surrounds negative electrode 21, positive electrode 22, and separator 18. Electrolyte composition 15 is ionically conductive, and includes a liquid solvent, in the present case, for example, a mixture of at least one cyclic carbonate (for example, ethylene carbonate (EC), propylene carbonate (PC), butylene carbonate (BC)), and at least one linear carbonate (for example, dimethylene carbonate (DMC), diethyl carbonate (DEC), methyl ethyl carbonate (MEC)), and a lithium salt (for example, $LiPF_6$, $LiBF_4$) and a compound of formula (III-c), where $E = -SO_2-C_6H_4-CH_3$, as additive. The quantity of additive is, for example, 2% by weight in each case, based on entire electrolyte composition 15.

The present invention is not limited to the exemplary embodiments described here and the aspects highlighted therein. Rather, numerous modifications within the range set forth herein are possible which are within the scope of activities carried out by those skilled in the art.

What is claimed is:

1. A hybrid supercapacitor, comprising:
at least one negative electrode that includes one of: a statically capacitive active material, an electrochemical redox active material, or a mixture of a statically capactivie active compound and an electrochemical redox active material;
at least one positive electrode that includes one of: a statically capacitive active material, an electrochemical redox active material, or a mixture of a statically capactivie active compound and an electrochemical redox active material;
at least one separator that is situated between the at least one negative electrode and the at least one positive electrode; and
an electrolyte composition;
wherein, at least one of negative and positive electrodes includes a statically capacitive active material, and at least one of the negative and positive electrodes includes an electrochemical redox active material;
wherein the electrolyte composition is a liquid electrolyte composition and includes at least one liquid, aprotic, organic solvent, at least one conducting salt, composed of at least one cation and at least one anion, that is suitable for balancing the charge of the cation, and at least one additive, selected from at least one Lewis acid, that is suitable for forming a complex compound with the at least one anion;
wherein the at least one additive includes a Lewis acid selected from a polydentate nitrogen compound.

2. The hybrid supercapacitor as recited in claim 1, wherein the at least one additive includes a Lewis acid selected from a boron(III) compound and an aluminum(III) compound.

3. The hybrid supercapacitor as recited in claim 1, wherein the at least one additive includes a boron(III) compound of formula (I):

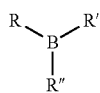

(I)

where
R, R', and R" may be independently selected from:
a hydrogen atom,
a halogen atom,
a hydroxy group,
a linear or branched, saturated or unsaturated, hydrocarbon moiety having either 1 to 18 carbon atoms or halogen atoms;
a cyclic, saturated or unsaturated, hydrocarbon moiety having 3 to 18 carbon, hydrogen atoms, or linear saturated alkyl moieties having 1 to 3 carbon atoms;
an aromatic hydrocarbon moiety having 6 to 18 carbon atoms, halogen atoms or linear, completely or partially fluorinated, saturated alkyl moieties having 1 to 3 carbon atoms; and
a moiety OR.

4. The hybrid supoercapacitor as recited in claim 3, wherein e adjacent moieties R, R', R" are joined together to form a cyclic compound.

5. The hybrid supercapacitor as recited in claim 1, wherein the polydentate nitrogen compound is a compound of formula (II):

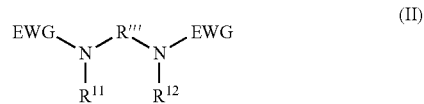

where
R'" represents at least one of an alkylene group —(CH$_2$)$_n$— having 1 to 10 carbon atoms (n=1 to 10), or at least one linear alkyl moiety having 1 to 6 carbon atoms, and at least one halogen atom;
EWG represents an electron-attracting group; and
$R^{11}$, $R^{12}$ independently represent a hydrogen atom, a linear or branched, saturated or unsaturated, alkyl moiety having 1 to 6 carbon atoms, an aryl moiety having 6 to 12 carbon atoms, or a moiety —R'"—NR$^3$(EWG), where R'" and EWG have the meanings defined above, and R$^3$ represents a further group $R^{11}$ or a further group R'", with the condition that $R^{11}$ and $R^{12}$ are joined together via this alkylene group R'" to form a cyclic compound.

6. The hybrid supercapacitor (2) as recited in claim 5, wherein the polydentate nitrogen compound is a cyclic compound of formula (III):

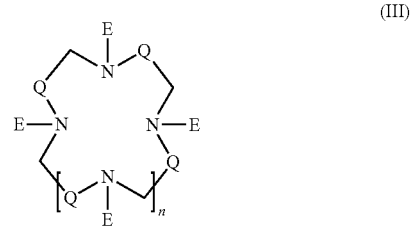

where
E represents an electron-attracting group selected from a tosyl group (—SO$_2$—C$_6$H$_4$—CH$_3$), a mesyl group (—SO$_2$—CH$_3$), and a triflyl group (—SO$_2$—CF$_3$);
Q represents an alkylene group of formula —(CH$_2$)$_m$— and m is an integer from 1 to 4; and
N represents an integer from 1 to 4.

7. The hybrid supercapacitor as recited in claim 1, wherein the at least one additive is a boron(III) compound of formula (I):

where
R, R', and R" may be independently selected from:
a hydrogen atom,
a halogen atom,
a hydroxy group,
a linear or branched, saturated or unsaturated, hydrocarbon moiety having either 1 to 18 carbon atoms or halogen atoms, a cyclic, saturated or unsaturated, hydrocarbon moiety having 3 to 18 carbon, hydrogen atoms, or linear saturated alkyl moieties having 1 to 3 carbon atoms, an aromatic hydrocarbon moiety having 6 to 18 carbon atoms, halogen atoms or linear, completely or partially fluorinated, saturated alkyl moieties having 1 to 3 carbon atoms, and a moiety OR;

wherein the boron(III) compound is in combination with a polydentate nitrogen compound wherein the polydentate nitrogen compound is a compound of formula (II):

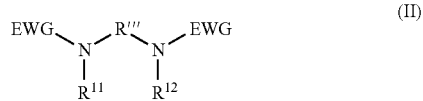

(II)

where

R''' represents at least one of an alkylene group —(CH$_2$)$_n$— having 1 to 10 carbon atoms (n=1 to 10), or at least one linear alkyl moiety having 1 to 6 carbon atoms, and at least one halogen atom;

EWG represents an electron-attracting group; and

R$^{11}$, R$^{12}$ independently represent a hydrogen atom, a linear or branched, saturated or unsaturated, alkyl moiety having 1 to 6 carbon atoms, an aryl moiety having 6 to 12 carbon atoms, or a moiety —R'''—NR$^3$(EWG), where R''' and EWG have the meanings defined above, and R$^3$ represents a further group R$^{11}$ or a further group R''', with the condition that R$^{11}$ and R$^{12}$ are joined together via this alkylene group R''' to form a cyclic compound.

8. The hybrid supercapacitor as recited in claim 1, wherein the at least one additive is added to the electrolyte composition in a quantity such that a molar ratio of conducting salt to additive of 1:0.5 to 1:5 is set.

9. An electrolyte composition for a hybrid supercapacitor, including at least one liquid, aprotic, organic solvent, at least one conducting salt, composed of at least one cation and at least one anion, that is suitable for balancing the charge of the cation, and at least one additive, selected from at least one Lewis acid, that is suitable for forming a complex compound with the at least one anion, wherein the Lewis acid is selected from a polydentate nitrogen compound.

10. The electrolyte composition as recited in claim 8, wherein the electrolyte composition is used in a hybrid supercapacitor.

* * * * *